United States Patent
Old et al.

(10) Patent No.: US 6,747,037 B1
(45) Date of Patent: Jun. 8, 2004

(54) PIPERIDINYL PROSTAGLANDIN E ANALOGS

(75) Inventors: David W. Old, Irvine, CA (US); Thang D. Dinh, Garden Grove, CA (US)

(73) Assignee: Allergan, Inc., Irvine, CA (US)

( * ) Notice: Subject to any disclaimer, the term of this patent is extended or adjusted under 35 U.S.C. 154(b) by 23 days.

(21) Appl. No.: 10/456,275

(22) Filed: Jun. 6, 2003

(51) Int. Cl.$^7$ ............... A61K 31/435; A61K 31/445; C07D 211/54; C07D 211/68; C07D 211/06

(52) U.S. Cl. ............... 514/277; 514/318; 514/319; 514/322; 514/324; 514/327; 546/24; 546/192; 546/193; 546/196; 546/202; 546/205; 546/210; 546/212; 546/213; 546/214; 546/216

(58) Field of Search ............... 546/24, 193, 194, 546/195, 196, 200, 205, 208, 216, 192, 202, 210, 212, 213, 244; 514/317, 318, 319, 320, 323, 326, 327, 322, 329, 277

(56) References Cited

U.S. PATENT DOCUMENTS

| | | | | |
|---|---|---|---|---|
| 4,299,970 A | * | 11/1981 | Cassidy et al. | 560/39 |
| 4,994,274 A | | 2/1991 | Chan et al. | 514/530 |
| 5,028,624 A | | 7/1991 | Chan et al. | 514/530 |
| 5,034,413 A | | 7/1991 | Chan et al. | 514/530 |
| 5,446,041 A | | 8/1995 | Chan et al. | 514/530 |

OTHER PUBLICATIONS

Bito, L.Z., *Biological Protection with Prostaglandins*, Cohen, M.M., ed., Boca Raton, Fla, CRC Press Inc., 1985, pp. 231–252.

Bito, L.Z., *Applied Pharmacology in the Medical Treatment of Glaucomas*, Drance, S.M. and Neufeld, A.H. eds, New York, Grune & Stratton, 1984, pp. 477–505.

Nilsson et al, Invest. *Ophthalmol. Vis. Sci.* (suppl), 284 (1987).

Bito, L.Z., *Arch. Ophthalmol.* 105, 1036 (1987).

Siebold et al, *Prodrug* 5 3 1989.

Huang et al, Synth. Commun., "Preparation of Optically Pure ω–Hydroxymethyl Lactams", 1989, 19, 3485–3496.

* cited by examiner

*Primary Examiner*—D. Margaret Seaman
*Assistant Examiner*—Raymond Covington
(74) *Attorney, Agent, or Firm*—Robert J. Baran; Martin A. Voet; Carlos A. Fisher

(57) ABSTRACT

The present invention provides a method of treating ocular hypertension or glaucoma which comprises administering to an animal having ocular hypertension or glaucoma therapeutically effective amount of a compound represented by the general formula I;

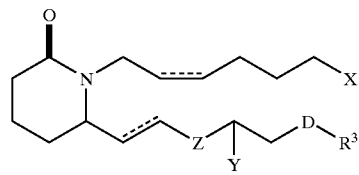

wherein X, Y, Z, D and $R^3$ are as defined in the specification.

21 Claims, No Drawings

PIPERIDINYL PROSTAGLANDIN E ANALOGS

FIELD OF THE INVENTION

The present invention relates to piperidinyl prostaglandin E analogs useful as therapeutic agents, e.g. ocular hypotensives that are particularly suited for the management of glaucoma.

BACKGROUND OF THE INVENTION

Description of Related Art

Ocular hypotensive agents are useful in the treatment of a number of various ocular hypertensive conditions, such as post-surgical and post-laser trabeculectomy ocular hypertensive episodes, glaucoma, and as presurgical adjuncts.

Glaucoma is a disease of the eye characterized by increased intraocular pressure. On the basis of its etiology, glaucoma has been classified as primary or secondary. For example, primary glaucoma in adults (congenital glaucoma) may be either open-angle or acute or chronic angle-closure. Secondary glaucoma results from pre-existing ocular diseases such as uveitis, intraocular tumor or an enlarged cataract.

The underlying causes of primary glaucoma are not yet known. The increased intraocular tension is due to the obstruction of aqueous humor outflow. In chronic open-angle glaucoma, the anterior chamber and its anatomic structures appear normal, but drainage of the aqueous humor is impeded. In acute or chronic angle-closure glaucoma, the anterior chamber is shallow, the filtration angle is narrowed, and the iris may obstruct the trabecular meshwork at the entrance of the canal of Schlemm. Dilation of the pupil may push the root of the iris forward against the angle, and may produce pupilary block and thus precipitate an acute attack. Eyes with narrow anterior chamber angles are predisposed to acute angle-closure glaucoma attacks of various degrees of severity.

Secondary glaucoma is caused by any interference with the flow of aqueous humor from the posterior chamber into the anterior chamber and subsequently, into the canal of Schlemm. Inflammatory disease of the anterior segment may prevent aqueous escape by causing complete posterior syn-cchia in iris bombe, and may plug the drainage channel with exudates. Other common causes are intraocular tumors, enlarged cataracts, central retinal vein occlusion, trauma to the eye, operative procedures and intraocular hemorrhage.

Considering all types together, glaucoma occurs in about 2% of all persons over the age of 40 and may be asymptotic for years before progressing to rapid loss of vision. In cases where surgery is not indicated, topical b-adrenoreceptor antagonists have traditionally been the drugs of choice for treating glaucoma.

Certain eicosanoids and their derivatives have been reported to possess ocular hypotensive activity, and have been recommended for use in glaucoma management. Eicosanoids and derivatives include numerous biologically important compounds such as prostaglandins and their derivatives. Prostaglandins can be described as derivatives of prostanoic acid which have the following structural formula:

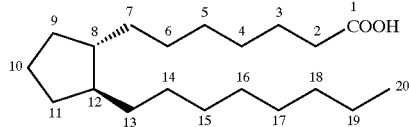

Various types of prostaglandins are known, depending on the structure and substituents carried on the alicyclic ring of the prostanoic acid skeleton. Further classification is based on the number of unsaturated bonds in the side chain indicated by numerical subscripts after the generic type of prostaglandin [e.g. prostaglandin $E_1$ ($PGE_1$), prostaglandin $E_2$ ($PGE_2$)], and on the configuration of the substituents on the alicyclic ring indicated by $\alpha$ or $\beta$ [e.g. prostaglandin $F_{2\alpha}$ ($PGF_{2\alpha}$)].

Prostaglandins were earlier regarded as potent ocular hypertensives, however, evidence accumulated in the last decade shows that some prostaglandins are highly effective ocular hypotensive agents, and are ideally suited for the long-term medical management of glaucoma (see, for example, Bito, L. Z. *Biological Protection with Prostaglandins*, Cohen, M. M., ed., Boca Raton, Fla., CRC Press Inc., 1985, pp. 231–252; and Bito, L. Z., *Applied Pharmacolopy in the Medical Treatment of Glaucomas* Drance, S. M. and Neufeld, A. H. eds., New York, Grune & Stratton, 1984, pp. 477–505. Such prostaglandins include $PGF_{2\alpha}$, $PGF_{1\alpha}$, $PGE_2$, and certain lipid-soluble esters, such as $C_1$ to $C_2$ alkyl esters, e.g. 1-isopropyl ester, of such compounds.

Although the precise mechanism is not yet known experimental results indicate that the prostaglandin-induced reduction in intraocular pressure results from increased uveoscleral outflow [Nilsson et.al., *Invest. Ophthalmol. Vis. Sci.* (suppl), 284 (1987)].

The isopropyl ester of $PGF_{2\alpha}$ has been shown to have significantly greater hypotensive potency than the parent compound, presumably as a result of its more effective penetration through the cornea. In 1987, this compound was described as "the most potent ocular hypotensive agent ever reported" [see, for example, Bito, L. Z., *Arch. Ophthalmol.* 105, 1036 (1987), and Siebold et.al., *Prodrup* 5 3 (1989)].

Whereas prostaglandins appear to be devoid of significant intraocular side effects, ocular surface (conjunctival) hyperemia and foreign-body sensation have been consistently associated with the topical ocular use of such compounds, in particular $PGF_{2\alpha}$ and its prodrugs, e.g., its 1-isopropyl ester, in humans. The clinical potentials of prostaglandins in the management of conditions associated with increased ocular pressure, e.g. glaucoma are greatly limited by these side effects.

In a series of co-pending United States patent applications assigned to Allergan, Inc. prostaglandin esters with increased ocular hypotensive activity accompanied with no or substantially reduced side-effects are disclosed. The co-pending U.S. Ser. No. 596,430 (filed Oct. 10, 1990, now U.S. Pat. No. 5,446,041), relates to certain 11-acyl-prostaglandins, such as 11-pivaloyl, 11-acetyl, 1-isobutyryl, 11-valeryl, and 11-isovaleryl $PGF_{2\alpha}$. Intraocular pressure reducing 15-acyl prostaglandins are disclosed in the co-pending application U.S. Ser. No. 175,476. (filed Dec. 29, 1993). Similarly, 11,15-9,15 and 9,11-diesters of prostaglandins, for example 11,15-dipivaloyl $PGF_{2\alpha}$ are known to have ocular hypotensive activity. See the co-pending patent applications U.S. Ser. No. 385,645 (filed Jul. 7, 1989, now U.S. Pat. No. 4,994,274), Ser. No. 584,370

(filed Sep. 18, 1990, now U.S. Pat. No. 5,028,624) and Ser. No. 585,284 (filed Sep. 18, 1990, now U.S. Pat. No. 5,034, 413). The disclosures of all of these patent applications are hereby expressly incorporated by reference.

SUMMARY OF THE INVENTION

The present invention concerns piperidinyl prostaglandin E analogues which are useful in a method of treating ocular hypertension which comprises administering to a mammal having ocular hypertension a therapeutically effective amount of a compound of formula I

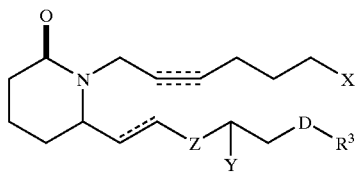

wherein hatched lines represent the α configuration, a triangle represents the β configuration, a wavy line represents either the α configuration or the β configuration and a dotted line represents the presence or absence of a double bond;

D represents a covalent bond or $CH_2$, O, S or NH;

X is $CO_2R$, $CONR_2$, $CH_2OR$, $P(O)(OR)_2$, $CONRSO_2R$, $SONR_2$ or

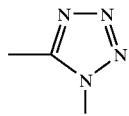

Y is $H^{\prime\prime\prime\prime}OR^1$, $R^1O^{\prime\prime\prime\prime}H$, $H^{\sim\sim}OR^1$ or O;

Z is $CH_2$ or a covalent bond;

R is H or $R^2$;

$R^1$ is H, $R^2$, phenyl, or $COR^2$;

$R^2$ is $C_1$–$C_5$ lower alkyl or alkenyl and $R^3$ is selected from the group consisting of $R^2$, phenyl, thienyl, furanyl, pyridyl, benzothienyl, benzofuranyl, naphthyl, or substituted derivatives thereof, wherein the substituents maybe selected from the group consisting of $C_1$–$C_5$ alkyl, halogen, $CF_3$, CN, $NO_2$, $NR_2$, $CO_2R$ and OR.

In a still further aspect, the present invention relates to a pharmaceutical product, comprising a container adapted to dispense its contents in a metered form; and an ophthalmic solution therein, as hereinabove defined.

Finally, certain of the compounds represented by the above formula, disclosed below and utilized in the method of the present invention are novel and unobvious.

DETAILED DESCRIPTION OF THE INVENTION

The present invention relates to the use of piperidinyl prostaglandin E therapeutic agents, e.g. as analogs as ocular hypotensives. The compounds used in accordance with the present invention are encompassed by the following structural formula I:

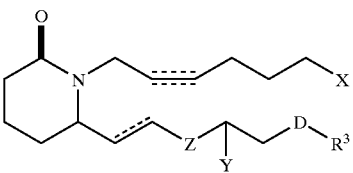

The preferred group of the compounds of the present invention includes compounds that have the following structural formula II.

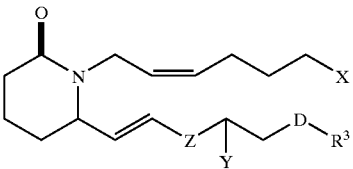

In the above formulae, the substituents and symbols are as hereinabove defined.

In the above formulae:

Preferably Y is

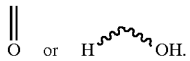

Preferably D represents a covalent bond or is $CH_2$; more preferably D is $CH_2$ and $R^3$ is n-propyl or D is a covalent bond and $R^3$ is phenyl.

Preferably Z represents a covalent bond.

Preferably R is H or $C_1$–$C_5$ lower alkyl.

Preferably $R^1$ is H.

Preferably $R^3$ is selected from the group consisting of phenyl and n-propyl.

Preferably X is $CO_2R$ and more preferably R is selected from the group consisting of H and methyl.

The above compounds of the present invention may be prepared by methods that are known in the art or according to the working examples below. The compounds, below, are especially preferred representative, of the compounds of the present invention.

7-[2-oxo-6-((E)-3-oxo-oct-1-enyl)-piperidin-1-yl]-hept-5-ynoic acid methyl ester 7-[2-oxo-6-((E)-3-oxo-oct-1-enyl)-piperidin-1-yl]-hept-5-ynoic acid (Z)-7-[2-oxo-6-((E)-3-oxo-oct-1-enyl)-piperidin-1-yl]-hept-5-enoic acid methyl ester (Z)-7-[2-oxo-6-((E)-3-oxo-oct-1-enyl)-piperidin-1-yl]-hept-5-enoic acid 7-[2-oxo-6-(3-oxo-octyl)-piperidin-1-yl]-heptanoic acid methyl ester 7-[2-oxo-6-(3-oxo-octyl)-piperidin-1-yl]-heptanoic acid 7-[2-(3-hydroxy-octyl)-6-oxo-piperidin-1-yl]-heptanoic acid methyl ester 7-[2-(3-hydroxy-octyl)-6-oxo-piperidin-1-yl]-heptanoic acid (Z)-7-[2-((E)-3-hydroxy-oct-1-enyl)-6-oxo-piperidin-1-yl]-hept-5-enoic acid methyl ester (Z)-7-[2-((E)-3-hydroxy-oct-1-enyl)-6-oxo-piperidin-1-yl]-hept-5-enoic acid 7-[2-oxo-6-((E)-3-oxo-oct-1-enyl)-piperidin-1-yl]-heptanoic acid methyl ester 7-[2-oxo-6-((E)-3-oxo-oct-1-enyl)-piperidin-1-yl]-heptanoic acid 7-[2-((E)-3-hydroxy-oct-1-enyl)-6-oxo-piperidin-1-yl]-heptanoic acid methyl ester 7-[2-((E)-3-hydroxy-oct-1-enyl)-6-oxo-piperidin-1-yl]-heptanoic acid 7-[2-oxo-6-((E)-3-oxo-4-phenyl-but-1-enyl)-piperidin-1-yl]-heptanoic acid methyl ester 7-[2-oxo-6-((E)-3-oxo-4-phenyl-but-1-enyl)-piperidin-1-yl]-heptanoic acid 7-[2-((E)-3-hydroxy-4-phenyl-but-1-enyl)-6-oxo-piperidin-1-yl]-heptanoic acid methyl ester 7-[2-((E)-3-hydroxy-4-phenyl-but-1-enyl)-6-oxo-piperidin-1-yl]-heptanoic acid 7-[2-(3-hydroxy-4-phenyl-butyl)-6-oxo-piperidin-1-yl]-heptanoic acid methyl ester 7-[2-(3-hydroxy-4-phenyl-butyl)-6-oxo-piperidin-1-yl]-heptanoic acid 7-[2-oxo-6-(3-oxo-4-phenyl-butyl)-piperidin-1-yl]-heptanoic acid methyl ester 7-[2-oxo-6-(3-oxo-4-phenyl-butyl)-piperidin-1-yl]-heptanoic acid 7-[2-oxo-6-((E)-3-oxo-4-phenyl-but-1-enyl)-piperidin-1-yl]-hept-5-ynoic acid methyl ester 7-[2-oxo-6-((E)-3-oxo-4-phenyl-but-1-enyl)-piperidin-1-yl]-hept-5-ynoic acid (Z)-7-[2-oxo-6-((E)-3-oxo-4-phenyl-but-1-enyl)-piperidin-1-yl]-hept-5-enoic acid methyl ester (Z)-7-[2-oxo-6-((E)-3-oxo-4-phenyl-but-1-enyl)-piperidin-1-yl]-hept-5-enoic acid (Z)-7-[2-((E)-3-hydroxy-4-phenyl-but-1-enyl)-6-oxo-piperidin-1-yl]-hept-5-enoic acid methyl ester (Z)-7-[2-((E)-3-hydroxy-4-phenyl-but-1-enyl)-6-oxo-piperidin-1-yl]-hept-5-enoic acid Pharmaceutical compositions may be prepared by combining a therapeutically effective amount of at least one compound according to the present invention, or a pharmaceutically acceptable acid addition salt thereof, as an active ingredient, with conventional ophthalmically acceptable pharmaceutical excipients, and by preparation of unit dosage forms suitable for topical ocular use. The therapeutically efficient amount typically is between about 0.0001 and about 5% (w/v), preferably about 0.001 to about 1.0% (w/v) in liquid formulations.

For ophthalmic application, preferably solutions are prepared using a physiological saline solution as a major vehicle. The pH of such ophthalmic solutions should preferably be maintained between 6.5 and 7.2 with an appropriate buffer system. The formulations may also contain conventional, pharmaceutically acceptable preservatives, stabilizers and surfactants.

Preferred preservatives that may be used in the pharmaceutical compositions of the present invention include, but are not limited to, benzalkonium chloride, chlorobutanol, thimerosal, phenylmercuric acetate and phenylmercuric nitrate. A preferred surfactant is, for example, Tween 80. Likewise, various preferred vehicles may be used in the ophthalmic preparations of the present invention. These vehicles include, but are not limited to, polyvinyl alcohol, povidone, hydroxypropyl methyl cellulose, poloxamers, carboxymethyl cellulose, hydroxyethyl cellulose and purified water.

Tonicity adjustors may be added as needed or convenient. They include, but are not limited to, salts, particularly sodium chloride, potassium chloride, mannitol and glycerin, or any other suitable ophthalmically acceptable tonicity adjustor.

Various buffers and means for adjusting pH may be used so long as the resulting preparation is ophthalmically acceptable. Accordingly, buffers include acetate buffers, citrate buffers, phosphate buffers and borate buffers. Acids or bases may be used to adjust the pH of these formulations as needed.

In a similar vein, an ophthalmically acceptable antioxidant for use in the present invention includes, but is not limited to, sodium metabisulfite, sodium thiosulfate, acetylcysteine, butylated hydroxyanisole and butylated hydroxytoluene.

Other excipient components which may be included in the ophthalmic preparations are chelating agents. The preferred chelating agent is edentate disodium, although other chelating agents may also be used in place or in conjunction with it.

The ingredients are usually used in the following amounts:

| Ingredient | Amount (% w/v) |
| --- | --- |
| active ingredient | about 0.001–5 |
| preservative | 0–0.10 |
| vehicle | 0–40 |
| tonicity adjustor | 1–10 |
| buffer | 0.01–10 |
| pH adjustor | q.s. pH 4.5–7.5 |
| antioxidant | as needed |
| surfactant | as needed |
| purified water | as needed to make 100% |

The actual dose of the active compounds of the present invention depends on the specific compound, and on the condition to be treated; the selection of the appropriate dose is well within the knowledge of the skilled artisan.

The ophthalmic formulations of the present invention are conveniently packaged in forms suitable for metered application, such as in containers equipped with a dropper, to facilitate the application to the eye. Containers suitable for dropwise application are usually made of suitable inert, non-toxic plastic material, and generally contain between about 0.5 and about 15 ml solution.

This invention is further illustrated by the following non-limiting Examples.

EXAMPLE 1

7-[2-oxo-6-((E)-3-oxo-oct-1-enyl)-piperidin-1-yl]-hept-5-ynoic acid methyl ester Step 1

6-(tert-butyl-dimethyl-silanyloxymethyl)-piperidin-2-one

Imidazole (1.16 g, 17.0 mmol) and tert-butyldimethylsilyl chloride (1.18 g, 7.85 mmol) were added sequentially to a solution of 6-hydroxymethyl-piperidin-2-one (prepared from racemic α-aminoadipic acid according to Huang, et al., *Synth. Commun.* 1989, 19, Preparation of Optically Pure ω-Hydroxymethyl Lactams, 3485–3496, 921 mg, 7.14 mmol) in DMF (10 mL) at 0° C. The reaction mixture was allowed to warm to rt and was stirred at rt for 17 h. Benzene and EtOAc (3:7, 200 mL) was added and the solution was washed with brine (3×50 mL). The organic phase was dried ($Na_2SO_4$), filtered and concentrated in vacuo. Purification of the residue by flash column chromatography on silica gel ($CH_2Cl_2 \rightarrow 3\%$ $MeOH/CH_2Cl_2$, gradient) afforded 1.53 g (88%) of 6-(tert-butyl-dimethyl-silanyloxymethyl)-piperidin-2-one as a white solid.

Step 2

7-[2-tert-butyl-dimethyl-silanyloxymethyl)-6-oxo-piperidin-1-yl]-hept-5-ynoic acid methyl ester Sodium hydride (60% dispersion in oil, 219 mg, 5.27 mmol) was added to a solution of 6-(tert-butyl-dimethyl-silanyloxymethyl)-piperidin-2-one (1.27 g, 5.21 mmol) in DMF (10 mL) at rt. After 1 h, methyl 7-iodohept-5-ynoate (1.52 g, 5.73 mmol) in DMF (2 mL) was added via cannula. After 18 h at rt, the reaction was quenched by the addition of aqueous HCl (0.5 M, 15 mL) and the mixture was extracted with EtOAc (3×30 mL). The combined organic phase was washed with brine (3×20 mL), dried ($Na_2SO_4$), filtered and concentrated in vacuo. Purification of the residue by flash column chromatography on silica gel ($CH_2Cl_2 \to 40\%$ $EtOAc/CH_2Cl_2$, gradient) afforded 1.04 g (53%) of 7-[2-tert-butyl-dimethyl-silanyloxymethyl)-6-oxo-piperidin-1-yl]-hept-5-ynoic acid methyl ester.

Step 3

7-(2-hydroxymethyl-6-oxo-piperidin-1-yl)-hept-5-ynoic acid methyl ester

Hydrogen fluoride-pyridine (2.5 mL) was added to a solution of 7-[2-tert-butyl-dimethyl-silanyloxymethyl)-6-oxo-piperidin-1-yl]-hept-5-ynoic acid methyl ester (1.07 g, 2.80 mmol) in acetonitrile (5.0 mL) in a plastic scintillation vial. After 3.5 h at rt, the reaction was quenched with saturated aqueous $NaHCO_3$ (70 mL) and the mixture was extracted with EtOAc (3×50 mL). The combined organic phase was washed with brine (50 mL), dried ($Na_2SO_4$), filtered and concentrated in vacuo. Purification of the residue by flash column chromatography on silica gel ($CH_2Cl_2 \to 3\%$ $MeOH/CH_2Cl_2$, gradient) afforded 724 mg (97%) of 7-(2-hydroxymethyl-6-oxo-piperidin-1-yl)-hept-5-ynoic acid methyl ester.

Step 4

7-(2-Formyl-6-oxo-piperidin-1-yl)-hept-5-ynoic acid methyl ester 1-(3-(Dimethylaminopropyl)-3-ethylcarbodiimide hydrochloride (EDCI, 530 mg, 2.76 mmol) and DMSO (0.26 mL, 3.68 mmol) were added sequentially to a solution of 7-(2-hydroxymethyl-6-oxo-piperidin-1-yl)-hept-5-ynoic acid methyl ester (246 mg, 0.92 mmol) in benzene (7.0 mL) at rt. The mixture was cooled to 0° C. and pyridinium trifluoroacetate (196 mg, 1.01 mmol) was added. The reaction was allowed to warm to rt and then was stirred at rt for 2.5 h. The solution was decanted from the oily residue and the residue was washed with benzene (3×5 mL). The combined benzene phases were concentrated in vacuo to afford crude 7-(2-formyl-6-oxo-piperidin-1-yl)-hept-5-ynoic acid methyl ester that was used without further purification.

Step 5

7-[2-oxo-6-((E)-3-oxo-oct-1-enyl)-piperidin-1-yl]-hept-5-ynoic acid methyl ester Sodium hydride (60% dispersion in oil, 37 mg, 0.91 mmol) was added to a solution of dimethyl 2-oxoheptylphosphonate (217 mg, 0.83 mmol) in THF (4 mL) at 0° C. After 10 min at 0° C., the solution was allowed to warm to rt. After 50 min at rt, the solution was recooled to 0° C. and 7-(2-formyl-6-oxo-piperidin-1-yl)-hept-5-ynoic acid methyl ester (crude from previous reaction, ~0.92 mmol) in THF (2 mL) was added via cannula. The reaction was allowed to warm to rt. After 18 h at rt, the reaction was quenched with acetic acid and water (1:1, 15 mL) and extracted with EtOAc (3×40 mL). The combined organic phase was washed with brine (50 mL), dried ($Na_2SO_4$), filtered and concentrated in vacuo. Purification of the residue by flash column chromatography on silica gel (10% $\to 50\%$ $EtOAc/CH_2Cl_2$, gradient) afforded 175 mg (58%) of the title compound.

EXAMPLE 2

7-[2-oxo-6-((E)-3-oxo-oct-1-enyl)-piperidin-1-yl]-hept-5-ynoic acid

Rabbit liver esterase (134 units/mg, 3 mg) was added to a solution of 7-[2-oxo-6-((E)-3-oxo-oct-1-enyl)-piperidin-1-yl]-hept-5-ynoic acid methyl ester (18 mg, 0.45 mmol) in acetonitrile (0.3 mL) and pH 7.2 phosphate buffer (3.0 mL). After 18.5 h, acetonitrile (10 mL) was added and the reaction mixture was concentrated to dryness in vacuo. Purification of the residue by flash column chromatography on silica gel ($CH_2Cl_2 \to 3\%$ $MeOH/CH_2Cl_2$, gradient) afforded 17 mg (97%) of the title compound.

EXAMPLE 3

(Z)-7-[2-oxo-6-((E)-3-oxo-oct-1-enyl)-piperidin-1-yl]-hept-5-enoic acid methyl ester A 50 mL round bottom flask was charged with nickel (II) chloride (273 mg, 2.10 mmol) and sodium borohydride (40 mg, 1.05 mmol), then 95% ethanol (2.0 mL) was added. The mixture immediately turned black. After 15 min at rt, ethylene diamine (0.23 mL, 3.36 mmol) was added. After another 15 min at rt, 7-[2-oxo-6-((E)-3-oxo-oct-1-enyl)-piperidin-1-yl]-hept-5-ynoic acid methyl ester (152 mg, 0.42 mmol) in 95% ethanol (2.0 mL) was added via cannula. A hydrogen atmosphere was established by evacuating and refilling with hydrogen (3×) and the reaction mixture was stirred under a balloon of hydrogen for 19 h. The reaction mixture was filtered through celite, washing with ethanol, and the filtrate was concentrated in vacuo. Purification of the resulting residue by flash column chromatography (10 $\to 50\%$ $EtOAc/CH_2Cl_2$, gradient) afforded 65 mg (43%) of the title compound.

EXAMPLE 4

(Z)-7-[2-oxo-6-((E)-3-oxo-oct-1-enyl)-piperidin-1-yl]-hept-5-enoic acid

In accordance with the procedure of example 2, (Z)-7-[2-oxo-6-((E)-3-oxo-oct-1-enyl)-piperidin-1-yl]-hept-5-enoic acid methyl ester (9 mg, 0.025 mmol) was converted into 5 mg (56%) of the title compound.

EXAMPLE 5

7-[2-oxo-6-(3-oxo-octyl)-piperidin-1-yl]-heptanoic acid methyl ester

Palladium on carbon (10 wt.%, 5 mg) was added to a solution of (Z)-7-[2-oxo-6-((E3-oxo-oct-1-enyl)-piperidin-1-yl]-hept-5-enoic acid methyl ester (40 mg, 0.11 mmol) in MeOH (3.0 mL). A hydrogen atmosphere was established by evacuating and refilling with hydrogen (3×) and the reaction mixture was stirred under a balloon of hydrogen for 19 h. The reaction mixture was filtered through celite, washing with MeOH, and the filtrate was concentrated in vacuo to afford 38 mg (94%) of the title compound.

EXAMPLE 6

7-[2-oxo-6-(3-oxo-octyl)-piperidin-1-yl]-heptanoic acid

In accordance with the procedure of example 2, 7-[2-oxo-6-(3-oxo-octyl)-piperidin-1-yl]-heptanoic acid methyl ester (14 mg, 0.038 mmol) was converted into 13 mg (97%) of the title compound.

EXAMPLE 7

7-[2-(3-hydroxy-octyl)-6-oxo-piperidin-1-yl]-heptanoic acid methyl ester

Sodium borohydride (24 mg, 0.63 mmol), followed by MeOH (2 drops), was added to a solution of 7-[2-oxo-6-(3-oxooctyl)-piperidin-1-yl]-heptanoic acid methyl ester (23 mg, 0.063 mmol) in $CH_2Cl_2$ (1.0 ML) at 0° C. The mixture was allowed to warm to rt. After 4 h at rt, the reaction was quenched with aqueous HCl (1.0 M) and extracted with EtOAc (3×10 mL). The combined organic phase was washed with saturated aqueous $NaHCO_3$ (15 mL) and brine (15 mL) then dried ($Na_2SO_4$), filtered and concentrated in vacuo. Purification of the residue by flash column chromatography on silica gel ($CH_2Cl_2 \times 3\%$ $MeOH/CH_2Cl_2$, gradient) afforded 14 mg (61%) of the title compound.

EXAMPLE 8

7-[2-(3-hydroxy-octyl)-6-oxo-piperidin-1-yl]-heptanoic acid

In accordance with the procedure of example 2, 7-[2-(3-hydroxy-octyl)-6-oxo-piperidin-1-yl]-heptanoic acid methyl ester (11.5 mg, 0.031 mmol) was converted into 6 mg (53%) of the title compound.

EXAMPLE 9

(Z)-7-[2-((E)-3-hydroxy-oct-1-enyl)-6-oxo-piperidin-1-yl]-hept-5enoic acid methyl ester In accordance with the procedure of example 7, (Z)-7-[2-oxo-6-((E)-3-oxo-oct-1-enyl)-piperidin-1-yl]-hept-5-enoic acid methyl ester (32 mg, 0.087 mmol) was converted into 25 mg (78%) of the title compound.

EXAMPLE 10

(Z)-7-[2-((E)-3-hydroxy-oct-1-enyl)-6-oxo-piperidin-1-yl]-hept-5-enoic acid

In accordance with the procedure of example 2, (Z)-7-[2-((E)-3-hydroxy-oct-1-enyl)-6-oxo-piperidin-1-yl]-hept-5-enoic acid methyl ester (10 mg, 0.028 mmol) was converted into 5 mg (52%) of the title compound.

EXAMPLE 11

7-[2-oxo-6-((E)-3-oxo-oct-1-enyl)-piperidin-1-yl]-heptanoic acid methyl ester

Step 1

7-(2-hydroxymethyl-6-oxo-piperidin-1-yl)-heptanoic acid methyl ester.

Palladium on carbon (10 wt.%, 20 mg) was added to a solution of 7-(2-hydroxymethyl-6-oxo-piperidin-1-yl)-hept-5-ynoic acid methyl ester (180 mg, 0.67 mmol) in MeOH (6.0 mL). A hydrogen atmosphere was established by evacuating and refilling with hydrogen (3×) and the reaction mixture was stirred under a balloon of hydrogen for 23 h. The reaction mixture was filtered through celite, washing with MeOH, and the filtrate was concentrated in vacuo to afford 184 mg (quant.) of 7-(2-hydroxymethyl-6-oxo-piperidin-1-yl)-heptanoic acid methyl ester.

Step 2

7-(2-Formyl-6-oxo-piperidin-1-yl)-heptanoic acid methyl ester.

EDCI (212 mg, 1.10 mmol) and DMSO (0.10 mL, 1.48 mmol) were added sequentially to a solution of 7-(2-hydroxymethyl-6-oxo-piperidin-1-yl)-heptanoic acid methyl ester (100 mg, 0.37 mmol) in benzene (4.0 mL) at rt. The mixture was cooled to 0° C. and pyridinium trifluoroacetate (79 mg, 0.41 mmol) was added. The reaction was allowed to warm to rt and then was stirred at rt for 3.5 h. The solution was decanted from the oily residue and the residue was washed with benzene (3×3 mL). The combined benzene phases were concentrated in vacuo to afford crude 7-(2-formyl-6-oxo-piperidin-1-yl)-heptanoic acid methyl ester that was used without further purification.

Step 3

7-[2-oxo-6-((E)-3-oxo-oct-1-enyl)-piperidin-1-yl]-heptanoic acid methyl ester

Sodium hydride (60% dispersion in oil, 15 mg, 0.37 mmol) was added to a solution of dimethyl 2-oxoheptylphosphonate (87 mg, 0.33 mmol) in THF (2 mL) at 0° C. After 10 min at 0° C., the solution was allowed to warm to rt. After 1 h at rt, the solution was recooled to 0° C. and 7-(2-formyl-6-oxo-piperidin-1-yl)-heptanoic acid methyl ester (crude from previous reaction, ~0.37 mmol) in THF (2 mL) was added via cannula. The reaction was allowed to warm to rt. After 17 h at rt, the reaction was quenched with acetic acid (50% aqueous, 20 mL) and extracted with EtOAc (3×20 mL). The combined organic phase was washed with saturated aqueous $NaHCO_3$ (20 mL) and brine (20 mL), dried ($Na_2SO_4$), filtered and concentrated in vacuo. Purification of the residue by flash column chromatography on silica gel ($CH_2Cl_2 \rightarrow 2\%$ $MeOH/CH_2Cl_2$, gradient) afforded 128 mg (95%) of the title compound.

EXAMPLE 12

7-[2-oxo-6-((E)-3-oxo-oct-1-enyl)-piperidin-1-yl]-heptanoic acid

In accordance with the procedure of example 2, 7-[2-oxo-6-((E)-3-oxo-oct-1-enyl)-piperidin-1-yl]-heptanoic acid methyl ester (17 mg, 0.048 mmol) was converted into 2 mg (12%) of the title compound after flash column chromatography on silica gel ($CH_2Cl_2 \rightarrow 2\%$ $MeOH/CH_2Cl_2$, gradient) and preparative thin layer chromatography (silica, 5% $MeOH/CH_2Cl_2$).

EXAMPLE 13

7-[2-((E)-3-hydroxy-oct-1-enyl)-6-oxo-piperidin-1-yl]-heptanoic acid methyl ester Sodium borohydride (42 mg, 1.10 mmol), followed by MeOH (0.38 mL), was added to a solution of 7-[2-oxo-6-((E)-3-oxo-oct-1-enyl)-piperidin-1-yl]-heptanoic acid methyl ester (40 mg, 0.11 mmol) in $CH_2Cl_2$ (1.13 mL) at 0° C. The mixture was allowed to warm to rt. After 3 h at rt, the reaction was quenched with aqueous HCl (1.0 M) and extracted with EtOAc (3×10 mL). The combined organic phase was washed with brine (20 mL) then dried ($Na_2SO_4$), filtered and concentrated in vacuo to afford 40 mg (99%) of the title compound.

EXAMPLE 14

7-[2-((E)-3-hydroxy-oct-1-enyl)-6-oxo-piperidin-1-yl]-heptanoic acid

In accordance with the procedure of example 2, 7-[2-((E)-3-hydroxy-oct-1-enyl)-6-oxo-piperidin-1-yl]-heptanoic acid methyl ester (18 mg, 0.049 mmol) was converted into 6 mg (35%) of the title compound.

EXAMPLE 15

7-[2-oxo-6-((E)-3-oxo-4-phenyl-but-1-enyl)-piperidin-1-yl]-heptanoic acid methyl ester Sodium hydride (60% dispersion in oil, 12 mg, 0.32 mmol) was added to a solution of dimethyl 2-oxo-3- phenylpropylphosphonate (70 mg, 0.29 mmol) in THF (1.5 mL) at 0° C. After 10 min at 0° C., the solution was allowed to warm to rt. After 50 min at rt, the solution was recooled to 0° C. and 7-(2-formyl-6-oxo-piperidin-1-yl)-heptanoic acid methyl ester (crude, prepared in accordance with example 11, step 2, ~0.32 mmol) in THF (1.5 mL) was added via cannula. The reaction was allowed to warm to rt. After 18 h at rt, the reaction was quenched with acetic acid (50% aqueous, 20 mL) and extracted with EtOAc (30×20 mL). The combined organic phase was washed with saturated aqueous $NaHCO_3$ (30 mL) and brine (30 mL), dried ($Na_2SO_4$), filtered and concentrated in vacuo. Purification of the residue by flash column chromatography on silica gel ($CH_2Cl_2 \rightarrow 2\%$ $MeOH/CH_2Cl_2$, gradient) afforded 66 mg (59%) of the title compound.

EXAMPLE 16

7-[2-oxo-6-((E)-3-oxo-4-phenyl-but-1-enyl)-piperidin-1-yl]-heptanoic acid

In accordance with the procedure of example 2, 7-[2-oxo-6-((E)-3-oxo-4-phenyl-but-1-enyl)-piperidin-1-yl]-heptanoic acid methyl ester (7 mg, 0.018 mmol) was converted into 2 mg (30%) of the title compound.

EXAMPLE 17

7-[2-((E)-3-hydroxy-4-phenyl-but-1-enyl)-6-oxo-piperidin-1-yl]-heptanoic acid methyl ester Sodium borohydride (36 mg, 0.96 mmol), followed by MeOH (0.25 mL), was added to a solution of 7-[2-oxo-6-((E)-3-oxo-4-phenyl-but-1-enyl)-piperidin-1-yl]-heptanoic acid methyl ester (37 mg, 0.096 mmol) in $CH_2Cl_2$ (0.75 mL) at 0° C. The mixture was allowed to warm to rt. After 1.5 h at rt, the reaction was quenched with aqueous HCl (1.0 M) and extracted with EtOAc (30×10 mL). The combined organic phase was washed with saturated aqueous $NaHCO_3$ (20 mL) and brine (20 mL) then dried ($Na_2SO_4$), filtered and concentrated in vacuo. Purification of the residue by flash column chromatography on silica gel ($CH_2Cl_2 \rightarrow 3\%$ $MeOH/CH_2Cl_2$, gradient) afforded 32 mg (86%) of the title compound.

EXAMPLE 18

7-[2-((E)-3-hydroxy-4-phenyl-but-1-enyl)-6-oxo-piperidin-1-yl]-heptanoic acid

In accordance with the procedure of example 2, 7-[2-((E)-3-hydroxy-4-phenyl-but-1-enyl)-6-oxo-piperidin-1-yl]-heptanoic acid methyl ester (10 mg, 0.026 mmol) was converted into 6.6 mg (68%) of the title compound.

EXAMPLE 19

7-[2-(3-hydroxy-4-phenyl-butyl)-6-oxo-piperidin-1-yl]-heptanoic acid methyl ester Palladium on carbon (10 wt.%, 5 mg) was added to a solution of 7-[2-((E)-3-hydroxy-4-phenyl-but-1-enyl)-6-oxo-piperidin-1-yl]-heptanoic acid methyl ester (20 mg, 0.052 mmol) in MeOH (2.0 mL). A hydrogen atmosphere was established by evacuating and refilling with hydrogen (3×) and the reaction mixture was stirred under a balloon of hydrogen for 22 h. The reaction mixture was filtered through celite, washing with MeOH, and the filtrate was concentrated in vacuo to afford 13 mg (65%) of the title compound.

EXAMPLE 20

7-[2-(3-hydroxy-4-phenyl-butyl)-6-oxo-piperidin-1-yl]-heptanoic acid

In accordance with the procedure of example 2, 7-[2-(3-hydroxy-4-phenyl-butyl)-6-oxo-piperidin-1-yl]-heptanoic acid methyl ester (11 mg, 0.029 mmol) was converted into 3.5 mg (32%) of the title compound.

EXAMPLE 21

7-[2-oxo-6-(3-oxo-4-phenyl-butyl)-piperidin-1-yl]-heptanoic acid methyl ester

In accordance with the procedure of example 19, 7-[2-oxo-6-((E)-3-oxo-4-phenyl-but-1-enyl)-piperidin-1-yl]-heptanoic acid methyl ester (20 mg, 0.052 mmol) was converted into 15 mg (75%) of the title compound.

EXAMPLE 22

7-[2-oxo-6-(3-oxo-4-phenyl-butyl)-piperidin-1-yl]-heptanoic acid

In accordance with the procedure of example 2, 7-[2-oxo-6-(3-oxo-4-phenyl-butyl)-piperidin-1-yl]-heptanoic acid methyl ester (12 mg, 0.031 mmol) was converted into 2.8 mg (24%) of the title compound.

EXAMPLE 23

7-[2-oxo-6-((E)-3-oxo-4-phenyl-but-1-enyl)-piperidin-1-yl]-hept-5-ynoic acid methyl ester Sodium hydride (60% dispersion in oil, 23 mg, 0.58 mmol) was added to a solution of dimethyl 2-oxo-3-phenylpropylphosphonate (171 mg, 0.64 mmol) in THF (2.0 mL) at 0° C. After 10 min at 0° C., the solution was allowed to warm to rt. After 50 min at rt, the solution was recooled to 0° C. and 7-(2-formyl-6-oxo-piperidin-1-yl)-hept-5-ynoic acid methyl ester (crude, prepared in accordance with example 1, step 4, ~0.64 mmol) in THF (2.0 mL) was added via cannula. The reaction was allowed to warm to rt. After 18 h at rt, the reaction was quenched with acetic acid (50% aqueous, 20 mL) and extracted with EtOAc (30×20 mL). The combined organic phase was washed with saturated aqueous $NaHCO_3$ (30 mL) and brine (30 mL), dried ($Na_2SO_4$), filtered and concentrated in vacuo. Purification of the residue by flash column chromatography on silica gel twice ($1^{st}$ $CH_2Cl_2 \rightarrow 2\%$ $MeOH/CH_2Cl_2$, gradient and $2^{nd}$ $CH_2Cl_2 \rightarrow 30\%$ $EtOAc/CH_2Cl_2$, gradient) afforded 51 mg (21%) of the title compound.

EXAMPLE 24

7-[2-oxo-6-((E)-3-oxo-4-phenyl-but-1-enyl)-piperidin-1-yl]-hept-5-ynoic acid

In accordance with the procedure of example 2, 7-[2-oxo-6-((E)-3-oxo-4-phenyl-but-1-enyl)-piperidin-1-yl]-hept-5-ynoic acid methyl ester (9 mg, 0.024 mmol) was converted into 1.4 mg (16%) of the title compound.

EXAMPLE 25

(Z)-7-[2-oxo-6-((E)-3-oxo-4-phenyl-but-1-enyl)-piperidin-1-yl]-hept-5-enoic acid methyl ester A round bottom flask was charged with nickel (II) chloride (68 mg, 0.52 mmol) and sodium borohydride (9.9 mg, 0.26 mmol), then 95% ethanol (1.0 mL) was added. The mixture immediately turned black. After 15 min at rt, ethylene diamine (56 µL, 0.84 mmol) was added. After another 15 min at rt, 7-[2-oxo-6-((E)-3-oxo-4-phenyl-but-1-enyl)-piperidin-1-yl]-hept-5-ynoic acid methyl ester (40 mg, 0.10 mmol) in 95% ethanol (1.0 mL) was added via cannula.

A hydrogen atmosphere was established by evacuating and refilling with hydrogen (3×) and the reaction mixture was stirred under a balloon of hydrogen for 18 h. The reaction mixture was filtered through celite, washing with ethanol, and the filtrate was concentrated in vacuo. Purification of the resulting residue by flash column chromatography ($CH_2Cl_2 \rightarrow 30\%$ $EtOAc/CH_2Cl_2$, gradient) afforded 28 mg (70%) of the title compound.

EXAMPLE 26

(Z)-7-[2-oxo-6-((E)-3-oxo-4-phenyl-but-1-enyl)-piperidin-1-yl]-hept-5-enoic acid In accordance with the procedure of example 2, (Z)-7-[2-oxo-6-((E)-3-oxo-4-phenyl-but-1-enyl)-piperidin-1-yl]-hept-5-enoic acid methyl ester (9.2 mg, 0.024 mmol) was converted into 8 mg (90%) of the title compound.

EXAMPLE 27

(Z)-7-[2-((E)-3-hydroxy-4-phenyl-but-1-enyl)-6-oxo-piperidin-1-yl]-hept-5-enoic acid methyl ester Sodium borohydride (16 mg, 0.42 mmol), followed by MeOH (0.25 mL), was added to a solution of (Z)-7-[2-oxo-6-((E)-3-oxo-4-phenyl-but-1-enyl)-piperidin-1-yl]-hept-5-enoic acid methyl ester (16 mg, 0.042 mmol) in $CH_2Cl_2$ (0.75 mL) at 0° C. The mixture was allowed to warm to rt. After 2.5 h at rt, the reaction was quenched with aqueous HCl (1.0 M) and extracted with EtOAc (3→15 mL). The combined organic phase was washed with saturated aqueous $NaHCO_3$ (15 mL) and brine (15 mL) then dried ($Na_2SO_4$), filtered and concentrated in vacuo. Purification of the residue by flash column chromatography on silica gel ($CH_2Cl_2 \rightarrow 50\%$ $EtOAc/CH_2Cl_2$, gradient) afforded 10 mg (62%) of the title compound.

EXAMPLE 28

(Z)-7-[2-((E)-3-hydroxy-4-phenyl-but-1-enyl)-6-oxo-piperidin-1-yl]-hept-5-enoic acid In accordance with the procedure of example 2, (Z)-7-[2-((E)-3-hydroxy-4-phenyl-but-1-enyl)-6-oxo-piperidin-1-yl]-hept-5-enoic acid methyl ester (8.5 mg, 0.022 mmol) was converted into 2.4 mg (29%) of the title compound.

These compounds are tested for in vitro activity as described below and the results given in the Table.

TABLE

| Example | Structure | Binding Data (IC50 in nM) | | | Functional Data (EC50 in nM) | | | | | | | |
|---|---|---|---|---|---|---|---|---|---|---|---|---|
| | | hEP2 | hEP30 | hEP4 | hFP | hEP1 | hEP2 | hEP3A | hEP4 | hTP | hP | hDP |
| 1 | 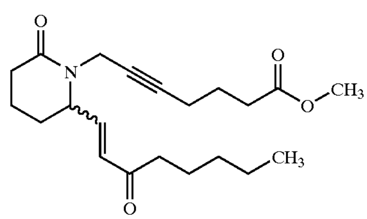 | | | | NA | NA | NA | NA | NA | >10000 | NA | |
| 2 | 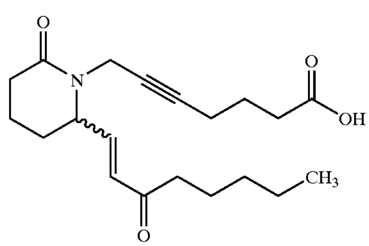 | | | | NA | NA | NA | NA | NA | | NA | |
| 3 | 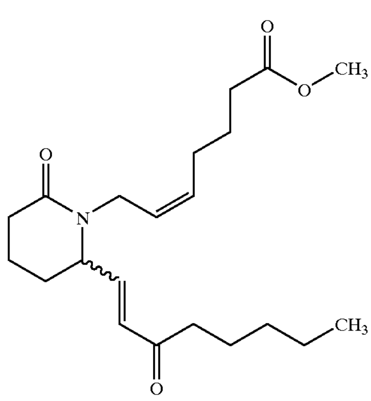 | | | | NA | NA | NA | NA | NA | | NA | |

TABLE-continued

| Example | Structure | Binding Data (IC50 in nM) | | | Functional Data (EC50 in nM) | | | | | | |
|---|---|---|---|---|---|---|---|---|---|---|---|
| | | hEP2 | hEP30 | hEP4 | hFP | hEP1 | hEP2 | hEP3A | hEP4 | hTP | hP | hDP |
| 4 | 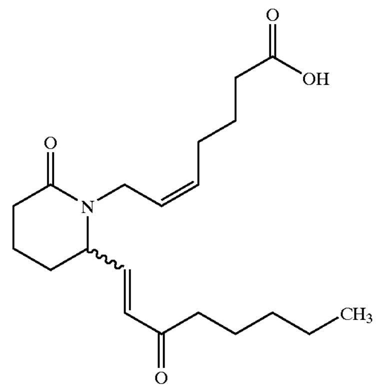 | | | | NA | NA | NA | NA | 10000 | | NA |
| 5 | 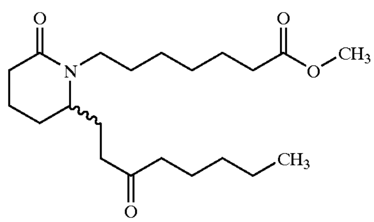 | | | | NA | NA | NA | NA | NA | >10000 | NA |
| 6 | 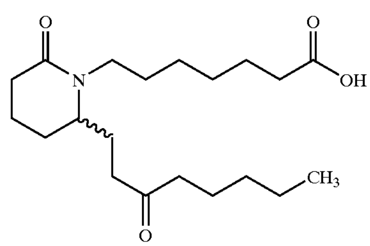 | | | | NA | NA | NA | NA | >10000 | | NA |
| 7 | 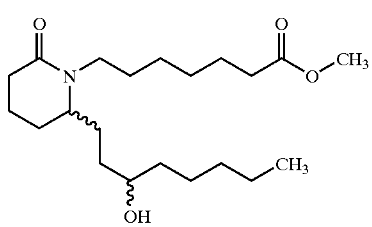 | | | | NA | NA | NA | NA | 1842 | >10000 | NA |
| 8 | 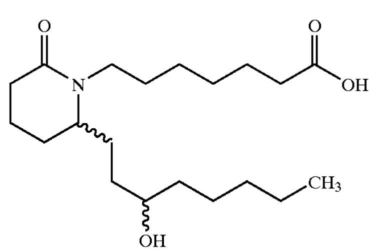 | | | | NA | NA | >10000 | | 99 | | |

TABLE-continued

| Example | Structure | Binding Data (IC50 in nM) | | | Functional Data (EC50 in nM) | | | | | | | |
|---|---|---|---|---|---|---|---|---|---|---|---|---|
| | | hEP2 | hEP30 | hEP4 | hFP | hEP1 | hEP2 | hEP3A | hEP4 | hTP | hP | hDP |
| 9 | 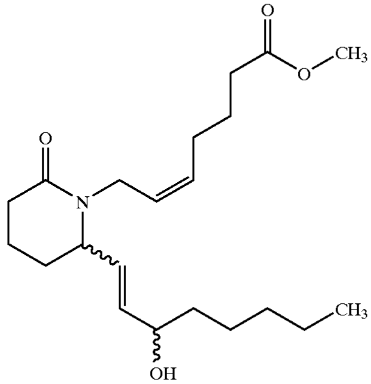 | | | | NA | NA | NA | NA | 815 | >10000 | NA | |
| 10 | 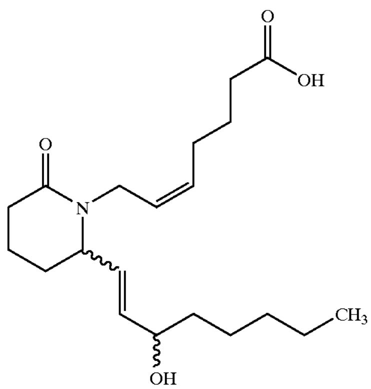 | | | | NA | >10000 | NA | | 46 | | NA | |
| 11 | 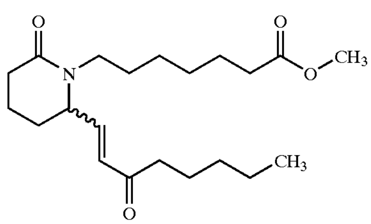 | | | | NA | NA | NA | NA | NA | >10000 | NA | |
| 12 | 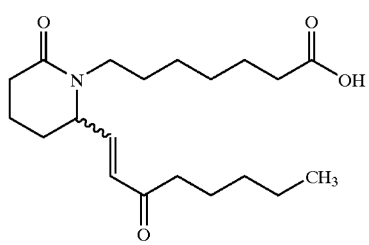 | | | | NA | NA | NA | NA | | | NA | |
| 13 | 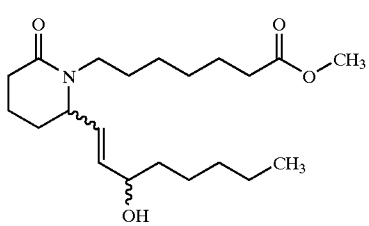 | | | | NA | NA | NA | NA | | NA | NA | |

TABLE-continued

| Example | Structure | Binding Data (IC50 in nM) | | | Functional Data (EC50 in nM) | | | | | | | |
|---|---|---|---|---|---|---|---|---|---|---|---|---|
| | | hEP2 | hEP30 | hEP4 | hFP | hEP1 | hEP2 | hEP3A | hEP4 | hTP | hP | hDP |
| 14 | 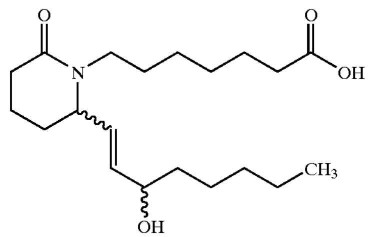 | | | | NA | NA | NA | | | >10000 | | |
| 15 | 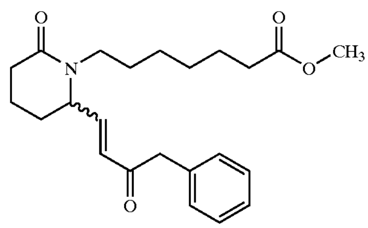 | | | | NA | NA | NA | NA | NA | >10000 | NA | |
| 16 | 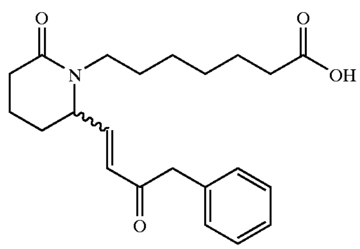 | | | | NA | NA | NA | NA | >10000 | | NA | |
| 17 | 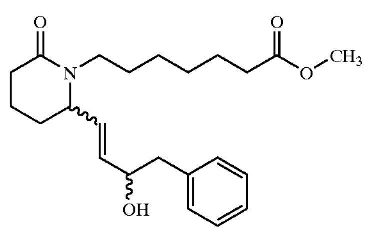 | | | | NA | NA | NA | NA | | NA | NA | |
| 18 | 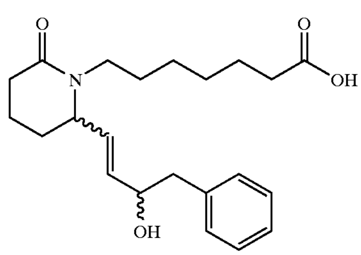 | | | | NA | NA | NA | NA | | NA | | |
| 19 | 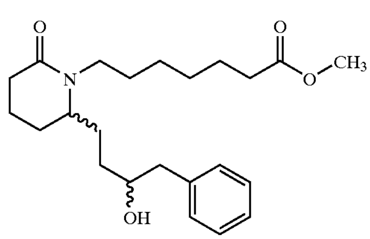 | | | | NA | NA | NA | NA | NA | >10000 | NA | |

TABLE-continued

| Example | Structure | Binding Data (IC50 in nM) | | | Functional Data (EC50 in nM) | | | | | | | |
|---|---|---|---|---|---|---|---|---|---|---|---|---|
| | | hEP2 | hEP30 | hEP4 | hFP | hEP1 | hEP2 | hEP3A | hEP4 | hTP | hP | hDP |
| 20 | 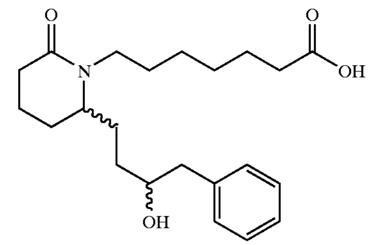 | | | | NA | NA | NA | NA | | NA | | |
| 21 | 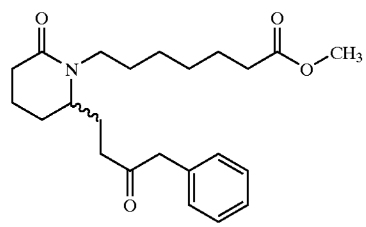 | | | | | | | | | | | |
| 22 | 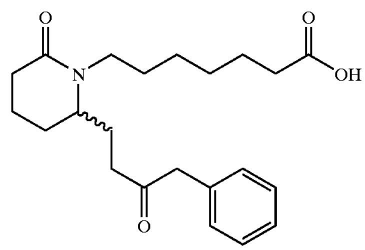 | | | | | | | | | | | |
| 23 | 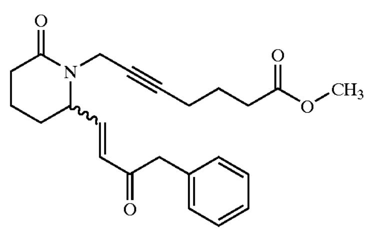 | | | | | | | | | | | |
| 24 | 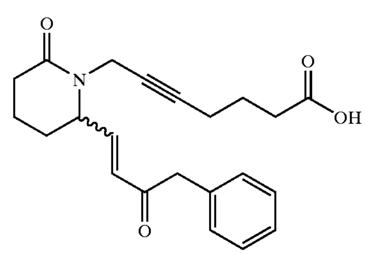 | | | | | | | | | | | |

US 6,747,037 B1

TABLE-continued

| Example | Structure | Binding Data (IC50 in nM) | | | Functional Data (EC50 in nM) | | | | | | | |
|---|---|---|---|---|---|---|---|---|---|---|---|---|
| | | hEP2 | hEP30 | hEP4 | hFP | hEP1 | hEP2 | hEP3A | hEP4 | hTP | hP | hDP |
| 25 | 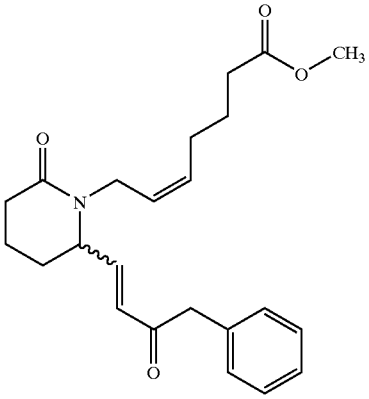 | | | | | | | | | | | |
| 26 | 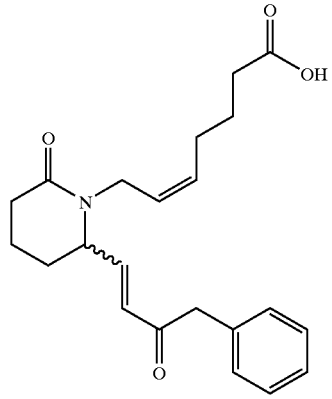 | | | | | | | | | | | |
| 27 | 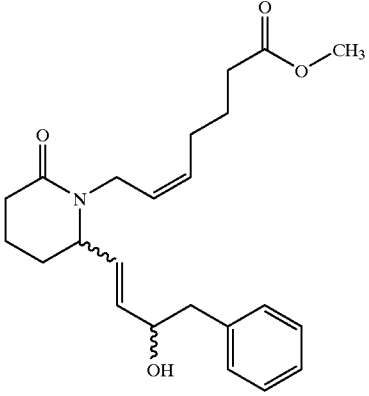 | | | | | | | | | | | |

Human Recombinant $EP_1$, $EP_2$, $EP_3$, $EP_4$, FP, TP, IP and DP Receptors: Stable Transfectants Plasmids encoding the human $EP_1$, $EP_2$, $EP_3$, $EP_4$, FP, TP, IP and DP receptors were prepared by cloning the respective coding sequences into the eukaryotic expression vector pCEP4 (Invitrogen). The pCEP4 vector contains an Epstein Barr virus (EBV) origin of replication, which permits episomal replication in primate cell lines expressing EBV nuclear antigen (EBNA-1). It also contains a hygromycin resistance gene that is used for eukaryotic selection. The cells employed for stable transfection were human embryonic kidney cells (HEK-293) that were transfected with and express the EBNA-1 protein. These HEK-293-EBNA cells (Invitrogen) were grown in medium containing Geneticin (G418) to maintain expression of the EBNA-1 protein. HEK-293 cells were grown in DMEM with 10% fetal bovine serum (FBS), 250 $\mu$g ml$^{-1}$ G418 (Life Technologies) and 200 $\mu$g ml$^{-1}$ gentamicin or penicillin/streptomycin. Selection of stable transfectants was achieved with 200 $\mu$g ml$^{-1}$ hygromycin, the optimal concentration being determined by previous hygromycin kill curve studies.

For transfection, the cells were grown to 50–60% confluency on 10 cm plates. The plasmid pCEP4 incorporating cDNA inserts for the respective human prostanoid receptor (20 μg) was added to 500 μl of 250 mM $CaCl_2$. HEPES buffered saline x2 (2xHBS, 280 mM NaCl, 20 mM HEPES acid, 1.5 mM $Na_2$ $HPO_4$, pH 7.05–7.12) was then added dropwise to a total of 500 μl, with continuous vortexing at room temperature. After 30 min, 9 ml DMEM were added to the mixture. The DNA/DMEM/calcium phosphate mixture was then added to the cells, which had been previously rinsed with 10 ml PBS. The cells were then incubated for 5 hr at 37° C. in humidified 95% air/5% $CO_2$. The calcium phosphate solution was then removed and the cells were treated with 10% glycerol in DMEM for 2 min. The glycerol solution was then replaced by DMEM with 10% FBS. The cells were incubated overnight and the medium was replaced by DMEM/10% FBS containing 250 μg $ml^{-1}$ G418 and penicillin/streptomycin. The following day hygromycin B was added to a final concentration of 200 μg $ml^{-1}$.

Ten days after transfection, hygromycin B resistant clones were individually selected and transferred to a separate well on a 24 well plate. At confluence each clone was transferred to one well of a 6 well plate, and then expanded in a 10 cm dish. Cells were maintained under continuous hygromycin selection until use.

Radioligand Binding

Radioligand binding studies on plasma membrane fractions prepared for cells stably transfected with the cat or human receptor were performed as follows. Cells washed with TME buffer were scraped from the bottom of the flasks and homogenized for 30 sec using a Brinkman PT 10/35 polytron. TME buffer was added as necessary to achieve a 40 ml volume in the centrifuge tubes. TME is comprised of 50 mM TRIS base, 10 mM $MgCl_2$, 1 mM EDTA; pH 7.4 is achieved by adding 1 N HCl. The cell homogenate was centrifuged at 19,000 rpm for 20–25 min at 4° C. using a Beckman Ti-60 or Tt-70 rotor. The pellet was then resuspended in TME buffer to provide a final protein concentration of 1 mg/ml, as determined by Bio-Rad assay. Radioligand binding assays were performed in a 100 μl or 200 μl volume.

The binding of $[^3H](N)$ $PGE_2$ (specific activity 165 Ci/mmol) was determined in duplicate and in at least 3 separate experiments. Incubations were for 60 min at 25° C. and were terminated by the addition of 4 ml of ice-cold 50 mM TRIS-HCl followed by rapid filtration through Whatman GF/B filters and three additional 4 ml washes in a cell harvester (Brandel). Competition studies were performed using a final concentration of 2.5 or 5 nM $[^3H](N)$ $PGE_2$ and non-specific binding was determined with $10^{-5}$ M unlabelled $PGE_2$.

For radioligand binding on the transient transfectants, plasma membrane fraction preparation was as follows. COS-7 cells were washed with TME buffer, scraped from the bottom of the flasks, and homogenized for 30 sec using a Brinkman PT 10/35 polytron. TME buffer was added to achieve a final 40 ml volume in the centrifuge tubes. The composition of TME is 100 mM TRIS base, 20 mM $MgCl_2$, 2M EDTA; 10N HCl is added to achieve a pH of 7.4.

The cell homogenate was centrifuged at 19000 rpm for 20 min at 4° C. using a Beckman Ti-60 rotor. The resultant pellet was resuspended in TME buffer to give a final 1 mg/ml protein concentration, as determined by Biorad assay. Radioligand binding assays were performed in a 200 μl volume.

The binding of $[^3H]$ $PGE_2$ (specific activity 165 Ci or $mmol^{-1}$) at $EP_{3D}$, receptors and $[^3H]$-SQ29548 (specific activity 41.5 Ci $mmol^{-1}$) at TP receptors were determined in duplicate in at least three separate experiments. Radiolabeled $PGE_2$ was purchased from Amersham, radiolabeled SQ29548 was purchased from New England Nuclear. Incubations were for 60 min at 25° C. and were terminated by the addition of 4 ml of ice-cold 50 mM TRIS-HC1, followed by rapid filtration through Whatman GF/B filters and three additional 4 ml washes in a cell harvester (Brandel). Competition studies were performed using a final concentration of 2.5 or 5 nM $[^3H]$-$PGE_2$, or 10 nM $[^3H]$-SQ 29548 and non-specific binding determined with 10 μM of the respective unlabeled prostanoid. For all radioligand binding studies, the criteria for inclusion were >50% specific binding and between 500 and 1000 displaceable counts or better.

The effects of the compounds of this invention on intraocular pressure may be measured as follows. The compounds are prepared at the desired concentrations in a vehicle comprising 0.1% polysorbate 80 and 10 mM TRIS base. Dogs are treated by administering 25 μl to the ocular surface, the contralateral eye receives vehicle as a control. Intraocular pressure is measured by applanation pneumatonometry. Dog intraocular pressure is measured immediately before drug administration and at 6 hours thereafter.

The compounds of this invention are useful in lowering elevated intraocular pressure in mammals, e.g. humans.

The foregoing description details specific methods and compositions that can be employed to practice the present invention, and represents the best mode contemplated. However, it is apparent for one of ordinary skill in the art that further compounds with the desired pharmacological properties can be prepared in an analogous manner, and that the disclosed compounds can also be obtained from different starting compounds via different chemical reactions. Similarly, different pharmaceutical compositions may be prepared and used with substantially the same result. Thus, however detailed the foregoing may appear in text, it should not be construed as limiting the overall scope hereof; rather, the ambit of the present invention is to be governed only by the lawful construction of the appended claims.

What is claimed is:

1. A method of treating ocular hypertension or glaucoma which comprises administering to an animal having ocular hypertension or glaucoma a therapeutically effective amount of a compound represented by the general formula

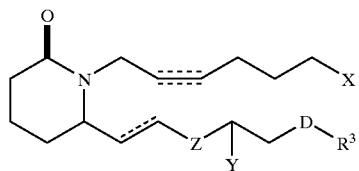

wherein hatched lines represent the α configuration, a triangle represents the β configuration, a wavy line represents either the α configuration or the β configuration and a dotted line represents the presence or absence of a double bond;

D represents a covalent bond or $CH_2$, O, S or NH;

X is $CO_2R$, $CONR_2$, $CH_2OR$, $P(O)(OR)_2$, $CONRSO_2R$, $SONR_2$ or

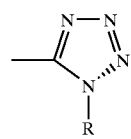

-continued

Y is 

Z is CH₂ or a covalent bond;
R is H or R²;
R¹ is H, R², phenyl, or COR²;
R² is C₁–C₅ lower alkyl or alkenyl and R₃ is selected from the group consisting of R², phenyl, thienyl, furanyl, pyridyl, benzothienyl, benzofuranyl, naphthyl, or substituted derivatives thereof, wherein the substituents maybe selected from the group consisting of C₁–C₅ alkyl, halogen, CF₃, CN, NO₂, NR2, CO₂R and OR.

2. The method according to claim 1 wherein said compound is represented by the general formula II;

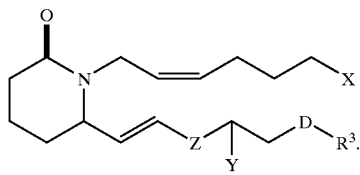

3. The method of claim 1 wherein Z represents a covalent bond.
4. The method of claim 1 wherein D is CH₂.
5. The method of claim 1 wherein X is CO₂R.
6. The method of claim 5 wherein R is selected from the group consisting of H and methyl.
7. The method of claim 5 wherein R is H, or C₁–C₅ alkyl.
8. The method of claim 1 wherein R₁ is H.
9. The method of claim 1 wherein R³ is selected from the group consisting of phenyl and n-propyl.
10. The method of claim 1 wherein said compound is selected from the group consisting of 7-[2-oxo-6-((E)-3-oxo-oct-1-enyl)-piperidin-1-yl]-hept-5-ynoic acid methyl ester,
7-[2-oxo-6-((E)-3-oxo-oct-1-enyl)-piperidin-1-yl]-hept-5-ynoic acid,
(Z)-7-[2-oxo-6-((E)-3-oxo-oct-1-enyl)-piperidin-1-yl]-hept-5-enoic acid methyl ester,
(Z)-7-[2-oxo-6-((E)-3-oxo-oct-1-enyl)-piperidin-1-yl]-hept-5-enoic acid,
7-[2-oxo-6-(3-oxo-octyl)-piperidin-1-yl]-heptanoic acid methyl ester,
7-[2-oxo-6-(3-oxo-octyl)-piperidin-1-yl]-heptanoic acid,
7-[2-(3-hydroxy-octyl)-6-oxo-piperidin-1-yl]-heptanoic acid methyl ester,
7-[2-(3-hydroxy-octyl)-6-oxo-piperidin-1-yl]-heptanoic acid,
(Z)-7-[2(E)-3-hydroxy-oct-1-enyl)-6-oxo-piperidin-1-yl]-hept-5-enoic acid methyl ester,
(Z)-7-[2-((E)-3-hydroxy-oct-1-enyl)-6-oxo-piperidin-1-yl]-hept-5-enoic acid,
7-[2-oxo-6-((E)-3-oxo-oct-1-enyl)-piperidin-1-yl]-heptanoic acid methyl ester,
7-[2-oxo-6-((E)-3-oxo-oct-1-enyl)-piperidin-1-yl]-heptanoic acid,
7-[2-((E)-3-hydroxy-oct-1-enyl)-6-oxo-piperidin-1-yl]-heptanoic acid methyl ester,
7-[2-((E)-3-hydroxy-oct-1-enyl)-6-oxo-piperidin-1-yl]-heptanoic acid,
7-[2-oxo-6-((E)-3-oxo-4-phenyl-but-1-enyl)-piperidin-1-yl]-heptanoic acid methyl ester,
7-[2-oxo-6-((E)-3-oxo-4-phenyl-but-1-enyl)-piperidin-1-yl]-heptanoic acid,
7-[2-((E)-3-hydroxy-4-phenyl-but-1-enyl)-6-oxo-piperidin-1-yl]-heptanoic acid methyl ester,
7-[2-((E)-3-hydroxy-4-phenyl-but-1-enyl)-6-oxo-piperidin-1-yl]-heptanoic acid,
7-[2-(3-hydroxy-4-phenyl-butyl)-6-oxo-piperidin-1-yl]-heptanoic acid methyl ester,
7-[2-(3-hydroxy-4-phenyl-butyl)-6-oxo-piperidin-1-yl]-heptanoic acid,
7-[2-oxo-6-(3-oxo-4-phenyl-butyl)-piperidin-1-yl]-heptanoic acid methyl ester,
7-[2-oxo-6-(3-oxo-4-phenyl-butyl)-piperidin-1-yl]-heptanoic acid,
7-[2-oxo-6-((E)-3-oxo-4-phenyl-but-1-enyl)-piperidin-1-yl]-hept-5-ynoic acid methyl ester,
7-[2-oxo-6-((E)-3-oxo-4-phenyl-but-1-enyl)-piperidin-1-yl]-hept-5-ynoic acid,
(Z)-7-[2-oxo-6-((E)-3-oxo-4-phenyl-but-1-enyl)-piperidin-1-yl]-hept-5-enoic acid methyl ester,
(Z)-7-[2-oxo-6-((E)-3-oxo-4-phenyl-but-1-enyl)-piperidin-1-yl]-hept-5-enoic acid,
(Z)-7-[2-((E)-3-hydroxy-4-phenyl-but-1-enyl)-6-oxo-piperidin-1-yl]-hept-5-enoic acid methyl ester and
(Z)-7-[2-((E)-3-hydroxy-4-phenyl-but-1-enyl)-6-oxo-piperidin-1-yl]-hept-5-enoic acid.

11. A compound represented by the general formula I;

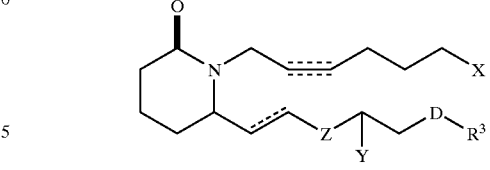

wherein hatched lines represent the α configuration, a triangle represents the β configuration, a wavy line represents either the α configuration or the β configuration and a dotted line represents the presence or absence of a double bond;

D represents a covalent bond or CH₂, O, S or NH;
X is CO₂R, CONR₂, CH₂OR, P(O)(OR)₂, CONRSO₂R, SONR₂ or

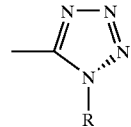

Y is 

Z is CH₂ or a covalent bond;
R is H or R²;
R¹ is H, R², phenyl, or COR²;
R² is C₁–C₅ lower alkyl or alkenyl and R₃ is selected from the group consisting of R², phenyl, thienyl, furanyl, pyridyl, benzothienyl, benzofuranyl, naphthyl, or substituted derivatives thereof, wherein the substituents maybe selected from the group consisting of C₁–C₅ alkyl, halogen, CF₃, CN, NO₂, NR₂, CO₂R and OR.

12. The compound according to claim 11 wherein said compound is represented by the general formula II;

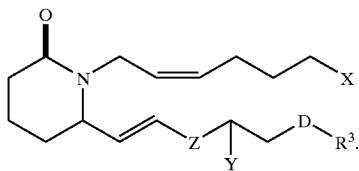

13. The compound of claim 11 wherein Z represents a covalent bond.

14. The compound of claim 11 wherein D is $CH_2$.

15. The compound of claim 11 wherein X is $CO_2R$.

16. The compound of claim 15 wherein R is selected from the group consisting of H and methyl.

17. The compound claim 15 wherein R is H, or $C_1$–$C_5$ alkyl.

18. The compound of claim 11 wherein $R_1$ is H.

19. The compound of claim 11 wherein $R^3$ is selected from the group consisting of phenyl and n-propyl.

20. The compound of claim 11 wherein said compound is selected from the group consisting of 7-[2-oxo-6-((E)-3-oxo-oct-1-enyl)-piperidin-1-yl]-hept-5-ynoic acid methyl ester,
7-[2-oxo-6-((E)-3-oxo-oct-1-enyl)-piperidin-1-yl]-hept-5-ynoic acid,
(Z)-7-[2-oxo-6-((E)-3-oxo-oct-1-enyl)-piperidin-1-yl]-hept-5-enoic acid methyl ester,
(Z)-7-[2-oxo-6-((E)-3-oxo-oct-1-enyl)-piperidin-1-yl]-hept-5-enoic acid,
7-[2-oxo-6-(3-oxo-octyl)-piperidin-1-yl]-heptanoic acid methyl ester,
7-[2-oxo-6-(3-oxo-octyl)-piperidin-1-yl]-heptanoic acid,
7-[2-(3-hydroxy-octyl)-6-oxo-piperidin-1-yl]-heptanoic acid methyl ester,
7-[2-(3-hydroxy-octyl)-6-oxo-piperidin-1-yl]-heptanoic acid,
(Z)-7-[2-((E)-3-hydroxy-oct-1-enyl)-6-oxo-piperidin-1-yl]-hept-5-enoic acid methyl ester,
(Z)-7-[2-((E)-3-hydroxy-oct-1-enyl)-6-oxo-piperidin-1-yl]-hept-5-enoic acid,
7-[2-oxo-6-((E)-3-oxo-oct-1-enyl)-piperidin-1-yl]-heptanoic acid methyl ester,
7-[2-oxo-6-((E)-3-oxo-oct-1-enyl)-piperidin-1-yl]-heptanoic acid,
7-[2-((E)-3-hydroxy-oct-1-enyl)-6-oxo-piperidin-1-yl]-heptanoic acid methyl ester,
7-[2-((E)-3-hydroxy-oct-1-enyl)-6-oxo-piperidin-1-yl]-heptanoic acid,
7-[2-oxo-6-((E)-3-oxo-4-phenyl-but-1-enyl)-piperidin-1-yl]-heptanoic acid methyl ester,
7-[2-oxo-6-((E)-3-oxo-4-phenyl-but-1-enyl)-piperidin-1-yl]-heptanoic acid,
7-[2-((E)-3-hydroxy-4-phenyl-but-1-enyl)-6-oxo-piperidin-1-yl]-heptanoic acid methyl ester,
7-[2-((E)-3-hydroxy-4-phenyl-but-1-enyl)-6-oxo-piperidin-1-yl]-heptanoic acid,
7-[2-(3-hydroxy-4-phenyl-butyl)-6-oxo-piperidin-1-yl]-heptanoic acid methyl ester,
7-[2-(3-hydroxy-4-phenyl-butyl)-6-oxo-piperidin-1-yl]-heptanoic acid,
7-[2-oxo-6-(3-oxo-4-phenyl-butyl)-piperidin-1-yl]-heptanoic acid methyl ester,
7-[2-oxo-6-(3-oxo-4-phenyl-butyl)-piperidin-1-yl]-heptanoic acid,
7-[2-oxo-6-((E)-3-oxo-4-phenyl-but-1-enyl)-piperidin-1-yl]-hept-5-ynoic acid methyl ester,
7-[2-oxo-6-((E)-3-oxo-4-phenyl-but-1-enyl)-piperidin-1-yl]-hept-5-ynoic acid,
(Z)-7-[2-oxo-6-((E)-3-oxo-4-phenyl-but-1-enyl)-piperidin-1-yl]-hept-5-enoic acid methyl ester,
(Z)-7-[2-oxo-6-((E)-3-oxo-4-phenyl-but-1-enyl)-piperidin-1-yl]-hept-5-enoic acid,
(Z)-7-[2-((E)-3-hydroxy-4-phenyl-but-1-enyl)-6-oxo-piperidin-1-yl]-hept-5-enoic acid methyl ester and
(Z)-7-[2-((E)-3-hydroxy-4-phenyl-but-1-enyl)-6-oxo-piperidin-1-yl]-hept-5-enoic acid.

21. An ophthalmic solution comprising a therapeutically effective amount of a compound represented by the general Formula 1

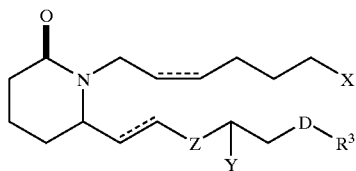

wherein hatched lines represent the α configuration, a triangle represents the β configuration, a wavy line represents the α configuration or the β configuration and a dotted line represents the presence or absence of a double bond;

D represents a covalent bond or $CH_2$, O, S or NH;

X is C $O_2R$, $CONR_2$, $CH_2OR$, $P(O)(OR)_2$, $CONRSO_2R$ $SONR_2$ or

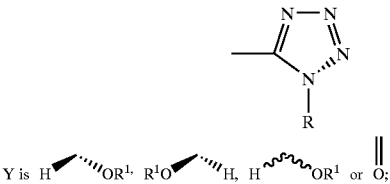

Y is H$^{\prime\prime\prime}$OR$^1$, R$^1$O$^{\prime\prime\prime}$H, H$^{\sim}$OR$^1$ or O;

Z is $CH_2$ or a covalent bond;

R is H or $R^2$;

$R^1$ is H, $R^2$, phenyl, or $COR^2$;

$R^2$ is $C_1$–$C_5$ lower alkyl or alkenyl and $R_3$ is selected from the group consisting of $R^2$, phenyl, thienyl, furanyl, pyridyl, benzothienyl, benzofuranyl, naphthyl or substituted derivatives thereof, wherein the substituents maybe selected from the group consisting of $C_1$–$C_5$ alkyl, halogen, $CF_3$, CN, $NO_2$, $NR_2$, $CO_2R$ and OR in admixture with a non-toxic, ophthalmically acceptable liquid vehicle, packaged in a container suitable for metered application.

* * * * *

UNITED STATES PATENT AND TRADEMARK OFFICE
CERTIFICATE OF CORRECTION

PATENT NO. : 6,747,037 B1
DATED : June 8, 2004
INVENTOR(S) : Old et al.

It is certified that error appears in the above-identified patent and that said Letters Patent is hereby corrected as shown below:

Title page,
Item [57], ABSTRACT,
Delete formula and insert in place thereof

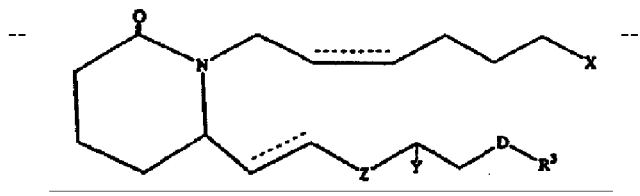

Column 1,
Lines 48-49, delete "syn-cchia" and insert in place thereof -- synechia --

Column 2,
Line 17, Delete "($PGF_{2\alpha}$)" and insert in place thereof -- ($PFG_{2\beta}$) --

Column 3,
Line 15, delete formula and insert in place thereof

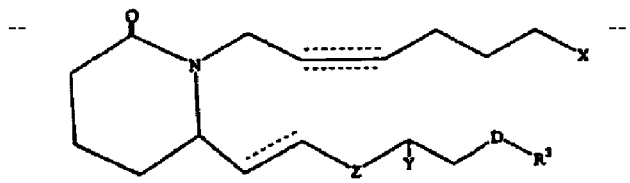

Line 52 delete "α" and insert in place thereof --a --

Column 4,
Line 1, delete formula and insert in place thereof

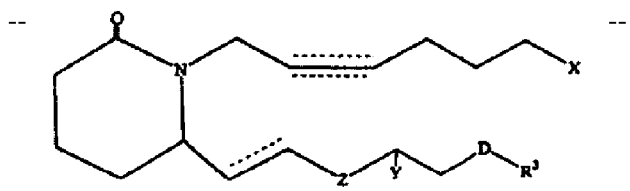

UNITED STATES PATENT AND TRADEMARK OFFICE
CERTIFICATE OF CORRECTION

PATENT NO. : 6,747,037 B1
DATED : June 8, 2004
INVENTOR(S) : Old et al.

Page 2 of 4

It is certified that error appears in the above-identified patent and that said Letters Patent is hereby corrected as shown below:

Column 4 (cont'd),
Line 15, delete formula and insert in place thereof

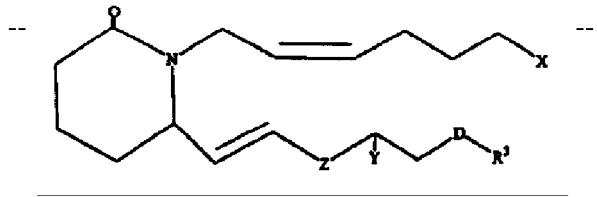

Column 8,
Line 51, delete "((E3-" and insert in place thereof -- ((E)-3- --

Column 9,
Line, delete "5enoic" and insert in place thereof -- 5-enoic --

Column 11,
Line 9, delete "(30 x 20" and insert in place thereof -- (3 x 20 --
Line 34, delete "(30 x 10 mL)" and insert in place thereof -- (3 x 20 mL) --

Column 12,
Line 37, delete "(30 x 20 mL)" and insert in place thereof -- (3 x 20 mL) --

Column 14,
Line 5, delete "(3→15 mL)" and insert in place thereof -- (3 x 15 mL) --

Column 26,
Line 45, delete formula and insert in place thereof

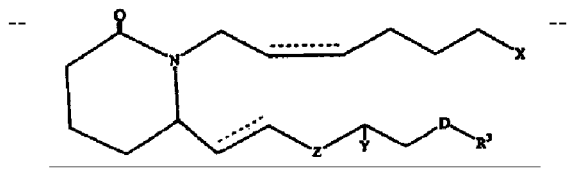

UNITED STATES PATENT AND TRADEMARK OFFICE
CERTIFICATE OF CORRECTION

PATENT NO. : 6,747,037 B1
DATED : June 8, 2004
INVENTOR(S) : Old et al.

It is certified that error appears in the above-identified patent and that said Letters Patent is hereby corrected as shown below:

Column 27,
Delete formula and insert in place thereof

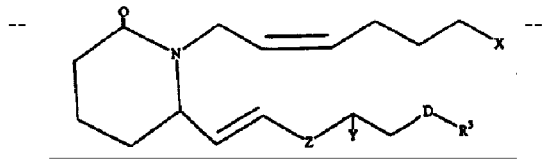

Line 14, delete "NR2" and insert in place thereof -- $NR_2$ --

Column 28,
Delete formula and insert in place thereof

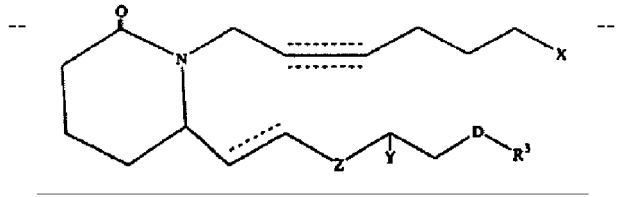

Column 29,
Line 5, delete formula and insert in place thereof

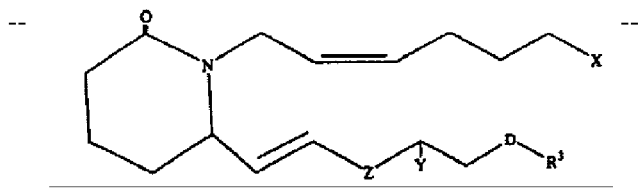

UNITED STATES PATENT AND TRADEMARK OFFICE
CERTIFICATE OF CORRECTION

PATENT NO. : 6,747,037 B1
DATED : June 8, 2004
INVENTOR(S) : Old et al.

It is certified that error appears in the above-identified patent and that said Letters Patent is hereby corrected as shown below:

Column 30,
Line 25, delete formula and insert in place thereof

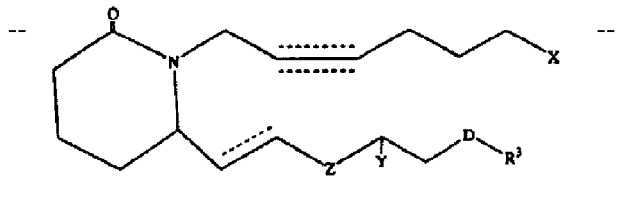

Signed and Sealed this

Fifteenth Day of March, 2005

JON W. DUDAS
*Director of the United States Patent and Trademark Office*